(12) United States Patent
Nielsen (10) Patent No.: US 9,707,373 B2
(45) Date of Patent: Jul. 18, 2017

(54) CATHETER ASSEMBLY

(71) Applicant: Arne Molgaard Nielsen, Copenhagen (DK)

(72) Inventor: Arne Molgaard Nielsen, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 28 days.

(21) Appl. No.: 13/787,242

(22) Filed: Mar. 6, 2013

(65) Prior Publication Data

US 2014/0074070 A1    Mar. 13, 2014

(30) Foreign Application Priority Data

Sep. 7, 2012 (EP) .................................. 12275135
Sep. 7, 2012 (GB) .................................. 1216005.7

(51) Int. Cl.
*A61M 25/00* (2006.01)
*A61B 17/00* (2006.01)
(Continued)

(52) U.S. Cl.
CPC ..... *A61M 25/005* (2013.01); *A61B 17/12181* (2013.01); *A61B 18/1492* (2013.01);
(Continued)

(58) Field of Classification Search
CPC ............ A61M 25/005; A61M 25/0054; A61M 2025/0059; A61M 2025/0062
(Continued)

(56) References Cited

U.S. PATENT DOCUMENTS 6,273,876 B1    8/2001    Klima et al.
7,909,812 B2    3/2011    Jansen et al.
(Continued)

FOREIGN PATENT DOCUMENTS

EP    0 439 931 A1    8/1991
EP    0 778 038 A2    6/1997
(Continued)

OTHER PUBLICATIONS

Duncan Graham-Rowe and Paul Marks, "Nano-Coated Implants Cut MRI Scan Dangers", New Scientist, Jun. 1, 2003 (Printed from Internet).
(Continued)

*Primary Examiner* — Rebecca E Eisenberg
(74) *Attorney, Agent, or Firm* — Eric D. Babych; Brinks Gilson & Lione (57) ABSTRACT

A catheter (40) or sheath (14) is provided with a strengthening element (30) embedded within the walls of the catheter (40). The strengthening element (30) is formed of a plurality of short strengthening members (32) arranged in longitudinally overlapping manner but which are radially spaced from one another and fixed to one another by annular coupling elements (36). The strengthening element (32) is made of a metal or metallic material, whereas the coupling elements (36) are made of a non-conductive material. The coupling elements (36) prevent electrical conduction through the length of the catheter (40) but retain a strengthening structure which provides torque strength and kink resistance. The short sections of conductive strengthening members (32) provide shielding of electromagnetic waves but prevent the strengthening element (30) acting as an aerial.

18 Claims, 4 Drawing Sheets

(51) Int. Cl.
*A61B 17/12* (2006.01)
*A61B 18/14* (2006.01)
*A61B 17/22* (2006.01)

(52) U.S. Cl.
CPC ............... *A61B 2017/00911* (2013.01); *A61B 2017/22001* (2013.01)

(58) Field of Classification Search
USPC .................................................. 604/523–526
See application file for complete search history.

(56) References Cited

U.S. PATENT DOCUMENTS

| 2007/0016165 A1 | 1/2007 | Von Oepen et al. |
| 2008/0058722 A1 | 3/2008 | Von Oepen et al. |
| 2011/0077678 A1 | 3/2011 | Ryan et al. |

FOREIGN PATENT DOCUMENTS

| EP | 1 712 247 A1 | 10/2006 |
| WO | WO 99/29360 | 6/1999 |

OTHER PUBLICATIONS

European Examination Report for Appln. No. 12 275 135.7 dated Jun. 19, 2015.
Search and Examination Report for Great Britain Patent Application Serial No. 1216005.7 dated Dec. 17, 2012, 5 pages.
Examination Report for Great Britain Patent Application Serial No. 1216005.7 dated Sep. 10, 2014, 1 page.
Extended Search Report for European Patent Application Serial No. 12 27 5135 dated Jan. 11, 2013, 5 pages.

CATHETER ASSEMBLY

This application claims the benefit of the filing date of United Kingdom (GB) patent application number 1216005.7, filed Sep. 7, 2012, and European Patent Office (EP) patent application number 12275315, filed Sep. 7, 2012, both of which are hereby incorporated by reference herein.

TECHNICAL FIELD

The present invention relates to a catheter assembly for a medical introducer device, suitable for any of the tubular elements of the device including for example the outer sheath, a device carrier, a delivery catheter and so on.

BACKGROUND ART

Introducer assemblies for delivering implantable medical devices or for carrying medical tools such as measuring devices endovascular within a patient are well known. These assemblies enable introduction of the assembly into a patient from a convenient percutaneous entry point, often far from the treatment site. For example, entry via the femoral artery is commonly effected for treatments within the aorta.

In order to ensure that the introducer assembly can be reliably pushed through a patient's vasculature, it is important that the assembly does not kink or otherwise collapse during its use, yet it must be sufficiently flexible to be able to pass through tortuous vascular paths without damaging the vessel walls, as well as being trackable, typically over a guide wire. Catheters, sheaths and the like are prone to kinking, particularly when they are made to curve to tight radii. Moreover, in order not to adversely affect any components carried in the catheter, it is important that the catheter retains a stable inner lumen, particularly as it is pushed through the patient's vasculature and as it is made to curve.

In order to meet such performance requirements it is common to strengthen such catheters, metal strengthening elements being optimal given their elastic and strength/volume properties. It has been found, however, that metal strengthening elements act as antennae, which makes them unsuitable for use with measuring devices. Moreover, such strengthening elements can lead to heating of the sheath as a result of currents induced in the elements during imaging, in effect as a result of noticeable SAR (specific absorption rate) characteristics.

Examples of prior art catheter assemblies can be found, for example, in U.S. Pat. No. 6,273,876 and U.S. Pat. No. 7,909,812.

An attempt to avoid the heating effect prevalent in such sheath assemblies, a reflective coating has been disclosed in "Nano-Coated Implants Cut MRI Scan Dangers" by Duncan Graham-Rowe and Paul Marks in New Scientist, 1 Jun. 2003.

DISCLOSURE OF THE INVENTION

The present invention seeks to provide an improved catheter assembly and catheter strengthening element. It is to be understood that the term catheter as used herein is intended to include all medical devices having the characteristics of a catheter, including outer sheaths of introducer assemblies, carrier and delivery catheters, balloon catheters, guide wire catheters and so on.

According to an aspect of the present invention, there is provided a catheter strengthening element having a longitudinal dimension and a radial dimension, the strengthening element including a plurality of metallic strengthening members disposed along a common axis, the strengthening members being radially spaced from one another by a radial space, with adjacent strengthening members partially overlapping one another in the longitudinal direction; the strengthening members being coupled together by at least one non-conductive coupling member. Advantageously, the strengthening members and annular coupling members form a unitary structure.

This structure of strengthening element ensures that metal or metal alloy can constitute a major part of the element, for the advantageous reasons indicated above, yet in a structure which allows the strengthening element to act as an electromagnetic shield but not as an aerial. In particular, a strengthening element which is continuous along the length of the catheter or at least greater than ¼ or ½ of the frequency of an imaging signal or communication signal can act as aerial within the catheter disrupting the correct operation of any measuring device carried in the catheter. In contrast, the preferred structures disclosed herein provide individual small sections of metallic strengthening members which are interconnected to one another in such a manner that torque can be transmitted from one member to the other and which is able to act as a shield to electromagnetic waves without acting as an aerial, thereby making the device safe for deploying measurement instruments. Furthermore, with segments which are of a length that they do not resonate with MR (or other) frequency, there is a reduction in heat generated (and SAR) during imaging, which can occur with catheters having continuous metallic strengthening elements. It is preferred, that the strengthening members have lengths less that ¼ or ½ of the frequency of electromagnetic imaging signals to be used with the catheter or the medical apparatus of which the catheter is a part.

Dividing a strengthening element into separate sections alone will not provide an adequate solution as this would leave weak zones between the strengthening sections as well as failing to provide a continuous electromagnetic shield important for correct operation of measuring devices. The structure proposed herein, on the other hand, provides non-metallic coupling or spacer members between the strengthening members or sections and such that they form a unitary structure with the strengthening members, minimising the chances of kinking. Thus, the structure of strengthening element taught herein can provide equivalent strengthening characteristics to a conventional all-metal strengthening element. Furthermore, the overlap between adjacent strengthening sections ensures a continuous electromagnetic shield.

In a preferred embodiment, the coupling members are operable to transmit radial compression and torque between two strengthening members to which they are coupled. The coupling members may have a flexibility comparable to the flexibility of the strengthening members. These characteristics, individually and in combination, can ensure that the structure can have analogous characteristics to an equivalent all-metal strengthening element, that is one having the same diameter and material thickness. It is not excluded that the coupling members could be made less flexible or more flexible than the strengthening members, to provide different performance characteristics to the strengthening element.

In an embodiment, the coupling members are made of a polymeric non-conductive material.

The strengthening members may be substantially tubular, and substantially cylindrical. In one embodiment, there are provided strengthening members of different diameters which are able to nest within one another.

It is preferred that the strengthening members are partially nested one within the other, and with each coupling member disposed radially outside one of the strengthening members and radially inside an adjacent partially nested strengthening member. This structure can ensure that when viewed in the longitudinal direction the strengthening element provide a continuous metal support providing an electromagnetic shield but one which is not formed of a single length of metal which can act as an antenna.

In the preferred embodiment, the strengthening members may be frusto-conical tubular elements.

Advantageously, the longitudinal overlap of adjacent strengthening members remains in being even when the strengthening element is curved, particularly to tight radii of curvature.

According to another aspect of the present invention, there is provided a catheter assembly including an inner layer providing a catheter lumen, a strengthening element disposed on the inner layer and an outer layer disposed over the strengthening element; the strengthening element having a longitudinal dimension and a radial dimension, the strengthening element including a plurality of metallic strengthening members disposed along a common axis, the strengthening members being radially spaced from one another by a radial space, with adjacent strengthening members partially overlapping one another in the longitudinal direction; the strengthening members being coupled together by at least one non-conductive coupling member.

Advantageously, the strengthening element provides a layer of the assembly distinct from the inner and outer layers.

The strengthening element can have any one or more of the characteristics taught herein.

The assembly may be one of a wire guide, a carrier or delivery catheter, a balloon catheter, an introducer sheath.

The teachings herein extend also to medical apparatus, such as an introducer assembly, including a catheter assembly as specified herein.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the drawings are schematic only and are not to scale. They are of a form which is intended to facilitate the understanding of the teachings herein.

Figure 1:
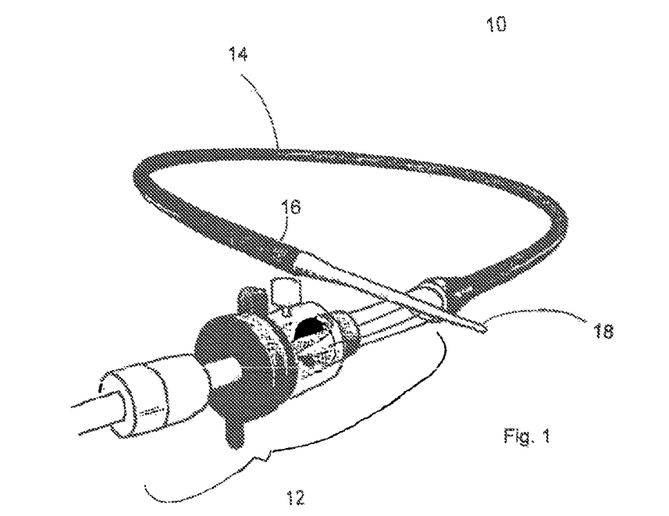
FIG. 1 is perspective view of an example of introducer assembly to which the teachings herein may be applied.

Referring first to FIG. 1, there is shown an example of introducer assembly 10 to which the teachings disclosed herein may be applied. It is to be understood, though, that the teachings herein may be applied to any catheters or other tubular medical elements, including outer sheaths of introducer assemblies, carrier catheters, delivery catheters, balloon catheters and so on.

The introducer assembly 10 of the example shown in FIG. 1 includes a proximal manipulation unit 12 which as is typical provides one or more haemostatic valves, one or more ports for supplying fluid to and/or from the assembly 10, one or more lumens for receiving internal catheters, guide wires, medical tools and so on.

Coupled to the proximal manipulation unit 12 is a sheath 14 which may typically have length from a few tens of centimeters to well over one meter. At the distal end 16 of the sheath 14 there is provided a dilator tip 18, of conventional form.

The introducer assembly 10 is typically deployed percutaneously into the patient and then endoluminally through the patient's vasculature up to the treatment site, which may be a significant distance from the percutaneous entry point. As will be appreciated from FIG. 1 and as is well known in the art, the introducer assembly 10, and in particular the parts thereof which are inserted into a patient, must be sufficiently flexible so as to be able to follow the path of the patient's vessels up to the treatment site without snagging against vessel walls and without excessive pressure to the vasculature.

As well as needing to be flexible, the sheath 14 will typically house or allow the passage therethrough of a number of medical or introducer components. For instance, the sheath may house a carrier catheter carrying an implantable medical device, a balloon catheter for angioplasty procedures, treatment devices, measurement devices, for effecting tumour ablation, for injecting contrast agent, for delivery of embolization materials and coils or other devices, and so on. It is important that the internal lumen of the sheath 14 does not narrow, distort or kink when the sheath 14 is curved, as so doing could damage the components housed within the sheath 14 or prevent their proper operation. It is also important for the sheath 14 to have as thin a wall as possible so as to minimise the footprint, or outer diameter, of the introducer assembly 10.

In order to address these issues, it is common for the sheath 14 to be of a multiple-component construction including a strengthening element embedded within smooth inner and outer layers.

Figure 2:
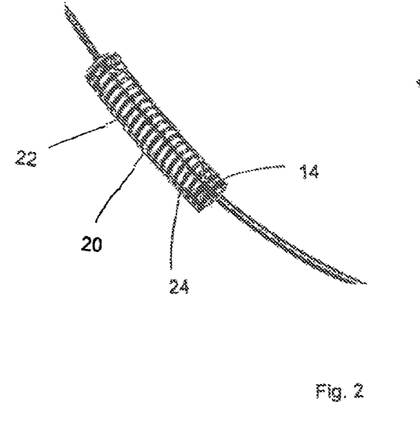
FIGS. 2 and 3 show two examples of strengthening structure of the introducer assembly of FIG. 1.

Referring now to FIG. 2, this shows one example of sheath 14, which includes outer and inner layers 20, 22, respectively, and sandwiched between the outer and inner layers 20, 22 a strengthening element 24. The strengthening element 24 may be in the form of a coil of flat wire made, typically of spring material such as spring steel. The strengthening element 24 advantageously extends along the entire length of the sheath 14.

The construction of sheath 14 shown in FIG. 2 is typically made by bonding the inner and outer layers 20, 22 to the strengthening element and also to one another, by heat or chemical (adhesive) bonding for instance, such that the structure is substantially unitary and solid. The spaces between the turns of coil 24 will typically be filled with material from one or both of the outer and inner layers 20, 22 or with adhesive or other bonding material.

The flexibility of the coil 24 allows the sheath 14 to be curved, as shown in FIG. 1, from a generally straight configuration, yet provides substantial strength against collapse and kinking of the sheath 14.

Figure 3:
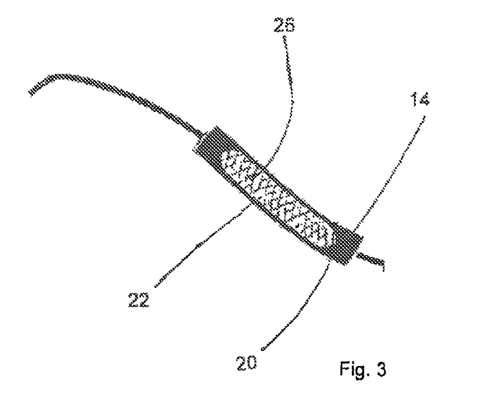

Referring now to FIG. 3, there is shown another example of construction for the sheath 14, in this Figure indicated by 14'. As with the example of FIG. 2, the sheath 14' includes an outer layer 20 and inner layer 22' which have sandwiched therebetween a strengthening element 26, in this example being a wire braid. The construction of the sheath 14' is in all other respects the same as the sheath 14 of FIG. 2. A braided strengthening element is typically more flexible than a coil of spring material, although may exhibit lower compression strength.

Optimum performance characteristics are attained with outer and inner layers made of a polymeric material and strengthening elements made of metal or metal alloy. However, metal or metallic strengthening elements which extend the whole length of the catheter can act as an aerial which can make them unsuitable for the deployment of measurement instruments. Furthermore, there is a risk that the catheter could heat up as a result of currents induced along the significant lengths of metal conductors by the electromagnetic energy produced during imaging.

The embodiments described below provide a structure of strengthening element for a catheter which has comparable structural characteristics than prior art catheter assemblies, yet which avoids the problems of prior art structures.

Figure 4:
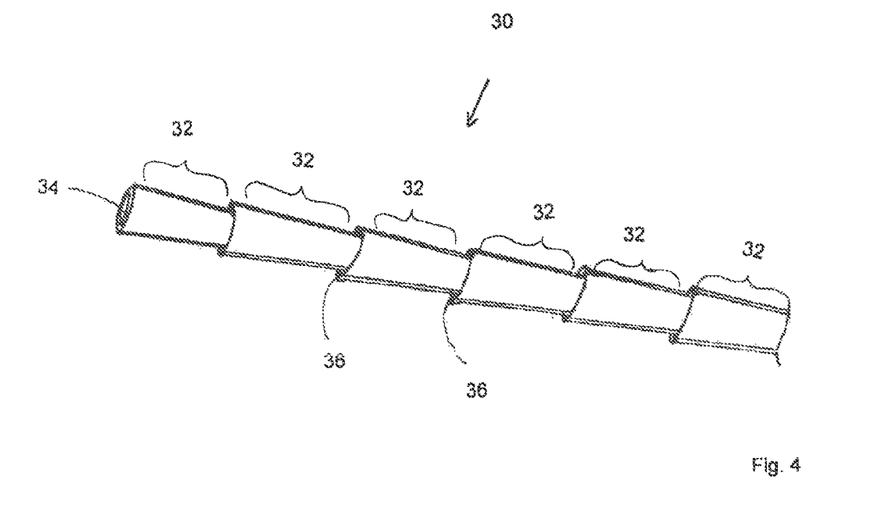
FIG. 4 is a perspective view of an embodiment of catheter strengthening element.

Referring first to FIG. 4, there is shown in schematic form a first embodiment of strengthening element for a catheter assembly. The strengthening element 30 includes a plurality of strengthening members or sections 32 arranged coaxially with respect to one another and providing a common internal lumen 34 passing through the strengthening members 32. Each strengthening member 32 is preferably formed of a braid, typically a braided wire. In the embodiment of FIG. 4, the strengthening elements 32 have a generally tapering or frusto-conical form, all in the same orientation such that the narrow end of one strengthening member 32 faces the wide end of its adjacent strengthening member 32. The strengthening members 32 are partially nested within one another, that is they overlap in the longitudinal direction of the assembly. The arrangement shown in FIG. 4 has the narrow end of one strengthening member 32 located within the wide end of the adjacent strengthening member 32, to overlap in the longitudinal direction of the element, such that there is no gap in the metal structure between the members 32 when viewed across the longitudinal direction of the assembly 30.

Each strengthening member 32 is preferably made of metal, metal alloy or other electrically conductive material, in the preferred embodiment of stainless steel, cobalt, chromium alloy, Nitinol or titanium. Each strengthening element may have a form and/or structure similar to that of the continuous strengthening elements of prior art catheters, preferably as a short length of braiding as shown in FIG. 3. In some embodiments, the strengthening members 32 may be made of solid metal, metal alloy or other metallic material with a frusto-conical shape.

The strengthening members 32 do not physically contact one another but are spaced from one another by an annular gap between the narrow end of one member 32 and the wide end of the adjacent strengthening member. Within these annular gaps there are provided annular coupling members 36 made of a non-conductive material, for example a polymer.

In addition to keeping adjacent strengthening members 32 electrically separated from one another, the coupling members 36 mechanically couple the strengthening members 32 together so that torque can be transmitted between the strengthening members 32 along the length of the element 30. The coupling members 36 also exhibit radial strength, keeping the overlapping sections 32 spaced from one another even when the element 10 is radially compressed or made to curve. The coupling members 36 are preferably made from a material which has sufficient strength to impart torque. Examples of suitable material include, but are not limited to: thermosetting or thermoplastic materials, nylon, polyurethane, polyethylene, and other materials used in catheter construction.

In the preferred embodiment the coupling members 36 are sufficiently strong to couple adjacent strengthening members 32 to one another in a substantially inelastic manner, and in particular to ensure that the overlap between adjacent strengthening members 32 remains, also on curving of the element 30 to tight radii of curvature. Furthermore, the coupling members 36 are advantageously made of a material which is able to fix or bond to the material structure of the strengthening members 32, for example by being moulded into the structure of the strengthening members, by being adhesively bonded or otherwise mechanically coupled thereto.

Figure 6:
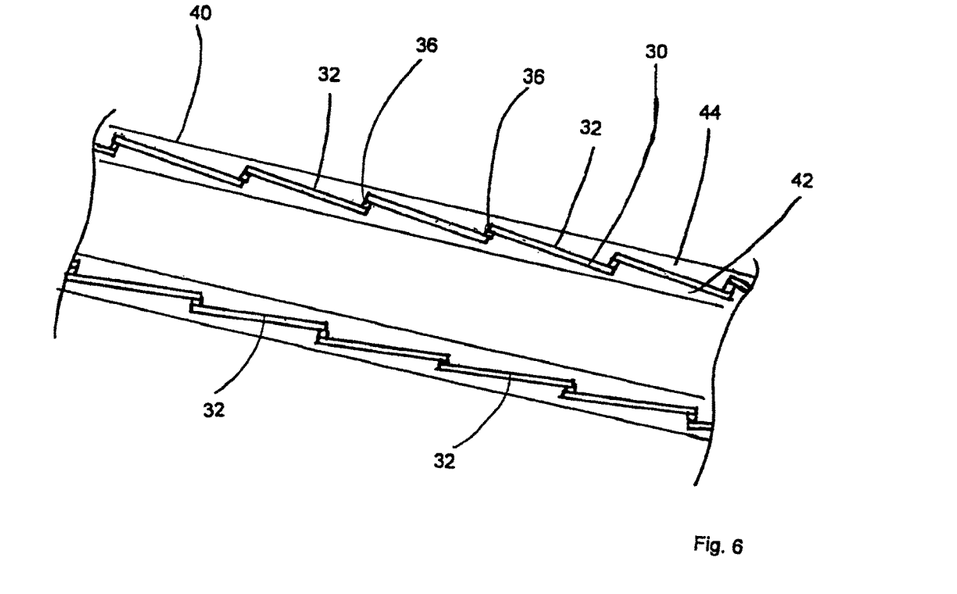
FIG. 6 is a longitudinal cross-sectional view of a catheter incorporating the catheter strengthening element of FIG. 4.

The assembly of strengthening members 32 and coupling members 36 advantageously creates a unitary structure which provides torque strength and a continuous metal surface when viewed from the side, as in FIGS. 4 and 6, to provide optimum shielding characteristics.

The radial space or gap between overlapping strengthening members 32 is preferably in the region of 0.01 mm to 0.5 mm. The overlap between adjacent strengthening elements 32 is preferably in the region of 0.5 mm to 2.0 mm. The annular coupling elements 36 have a width to fill the gap and a preferably length equivalent to the length of overlap, between around 0.5 mm to around 2.0 mm.

Referring now to FIG. 6, the strengthening element 30 can be seen embedded within the material of a sheath 40 so as to be located preferably entirely within the thickness of the wall of the catheter of the sheath 40. In practice, the catheter or sheath 40 could be formed of inner and outer layers 42 and 44, respectively, which sandwich the strengthening element 30 therebetween. The inner and outer layers 42, 44 may be provided as physically separate layers which are then coupled or bonded to one another during manufacture of the catheter or sheath 40 so as to form a unitary structure. In such an embodiment bonding may be by heating the assembly sufficiently to cause the layers 42 and 44 to melt or reflow, or may be by means of a suitable bonding agent. In some embodiments, the inner and outer layers, 42 and 44 could be in effect a single layer within which the strengthening element 30 is embedded during manufacture.

The strengthening members 32, coupled to one another by the spacer elements 36, provide strengthening of the catheter or sheath 40 preferably to an extent at least comparable to single continuous strengthening elements. However, the strengthening members 32, being of reduced length, are such as not to resonate at magnetic resonance (MR) frequencies used by MRI apparatus in a manner as to act as an aerial, and are of a size which absorb only minimal energy so as not to be heated excessively by any electromagnetic energy from imaging wages.

The structure of strengthening assembly 30 is such that the adjacent strengthening members 32 retain their longitudinal overlap both when the catheter or sheath 40 is substantially straight and also when it is curved to radii often experienced during the use of the catheter or sheath 40. This can be in part by use of spacer elements 36 which are sufficiently rigid to allow little movement between adjacent strengthening members 32 and/or by ensuring there is sufficient overlap of adjacent strengthening members 32 such that when the assembly 30 is curved any consequential relative movement of the strengthening members 32 caused by such curvature would not be enough to cause the adjacent strengthening members 32 to separate from one another so as to leave a longitudinal gap between them. In practice, it is preferred that any such flexibility between the coupling elements 36 is minimal so as to prevent any noticeable movement between the strengthening members which it connects together. It is preferred in this regard, that the flexibility of the strengthening element 30 is provided by the members 32 themselves rather than any coupling element between the members 32.

The use of metal, metal alloy or other metallic material for the strengthening members 32 reduces the required volume and in particular thickness of the strengthening element 30, as well as providing electromagnetic shielding to make it MR safe, without the risk of the structure acting as an antenna particularly at the magnetic RF field generated during magnetic resonance imaging. These characteristics make the catheter or sheath optimal for deploying measurement instruments.

Figure 5:
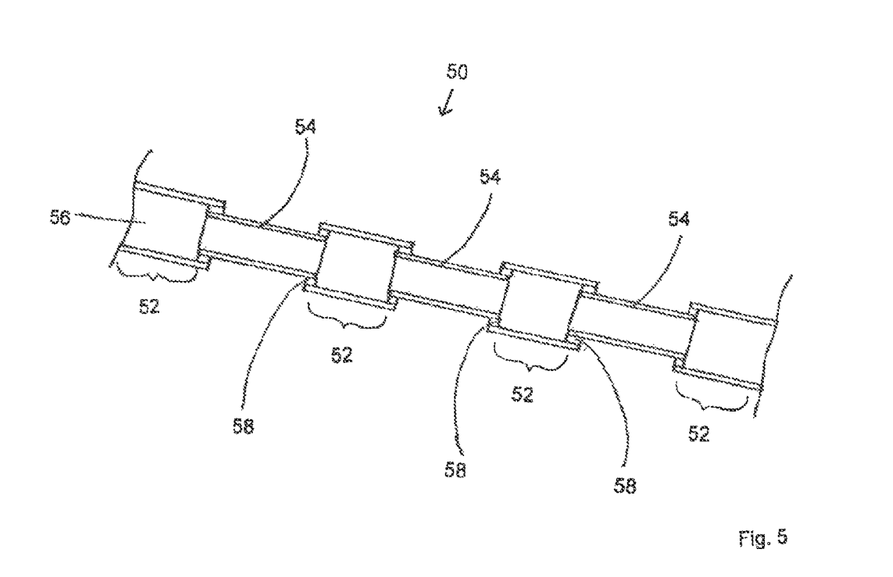
FIG. 5 is a perspective view of another embodiment of catheter strengthening element.

The structure of strengthening element 30 showed embodiments of FIGS. 4 and 5 is only one example of suitable structure. Another example is shown in FIGS. 5 and 7, which depict, respectively, cross-sectional views of a strengthening element and of a catheter or sheath.

Referring to FIG. 5 first, the embodiment of strengthening element 50 includes a plurality of first strengthening members or sections 52 having a first diameter and a plurality of second strengthening members 54 having a second diameter which is smaller than that of the first strengthening members 52. The strengthening members 52, 54 are arranged co-axially so as to provide a common lumen 56 therethrough. The members 52, 54 are interdigitated, such that each member of one type 52/54 is disposed between two members of the other type 54/52 and vice versa.

As will be apparent from FIG. 5, the strengthening members 52, 54 overlap longitudinally with one another but are radially spaced from one another, the gap being filled by annular coupling or spacer elements 58, having characteristics equivalent to the coupling or spacer elements 36 of the embodiments of FIGS. 4 and 6.

Figure 7:
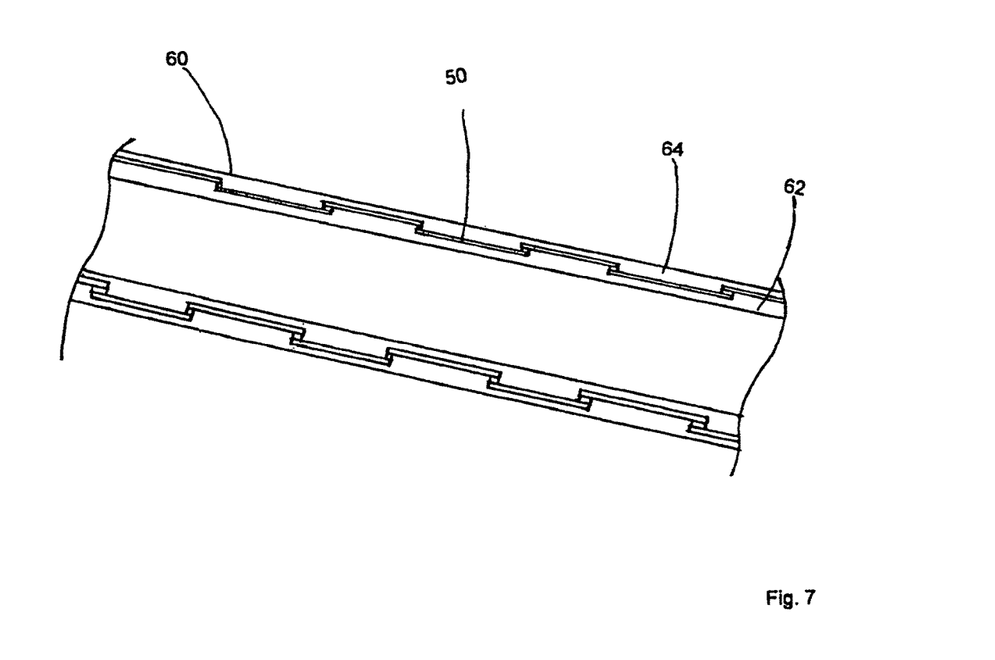
FIG. 7 is a longitudinal cross-sectional view of a catheter incorporating the catheter strengthening element of FIG. 5.

Referring to FIG. 7, the strengthening element 50 can be seen embedded within the walls of a catheter or sheath 60, which can be described as having inner and outer layers 62, 64, equivalent to the inner and outer layers 42, 44 of the catheter or sheath 40 of FIG. 6. The only difference between the catheter 60 and the catheter 40 is the type of strengthening element embedded therewithin.

Figure 8:
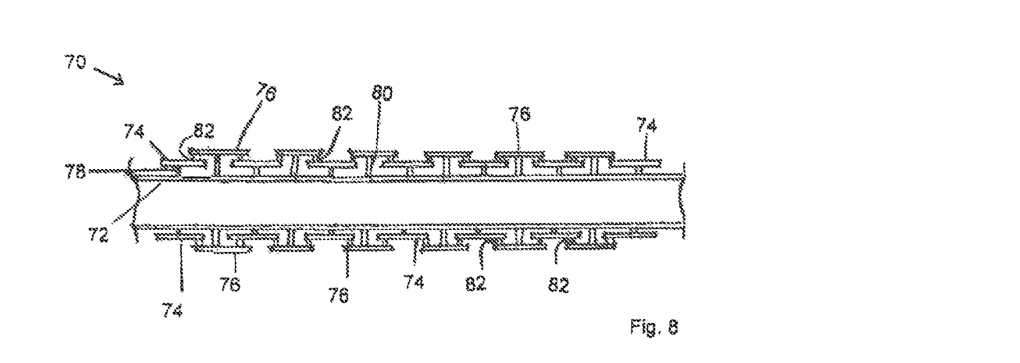
FIGS. 8 to 10 show cross-sectional views of a part of other embodiments of catheter strengthening element.
Figure 9:
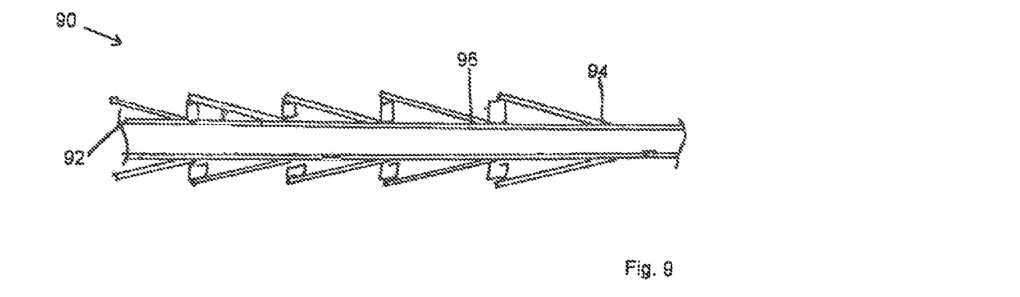
Figure 10:
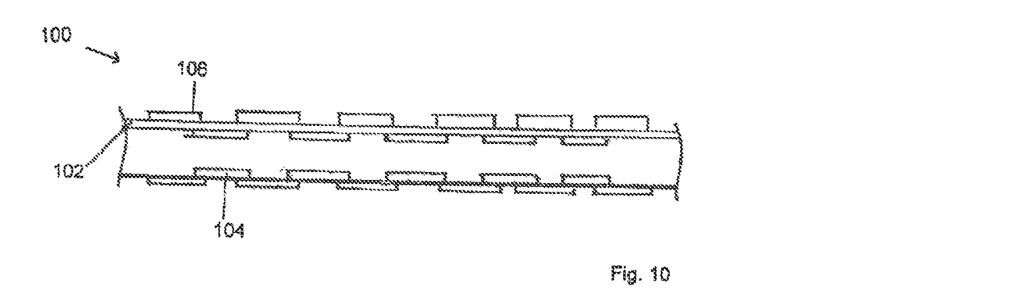

FIGS. 8 to 10 show different embodiments of strengthening elements which can be incorporated into a catheter assembly in the same manner as the embodiments described above. The skilled person will appreciate that the views in FIGS. 8 to 10 are not to scale and that in practice the strengthening elements will be constructed to have a small a thickness as possible in order to minimise the thickness of the catheter wall.

Referring first to FIG. 8, this shows an embodiment of strengthening element 70 in longitudinal cross-section. The strengthening element includes a tubular substrate 72 made of a non-conductive material. The assembly also includes first and second sets of annular strengthening members 74, 76. The first set of strengthening members 74 has a first diameter smaller than the diameters of the second set of strengthening members 76. The strengthening members 74, 76 are arranged coaxially with the tubular substrate 72 and interdigitated manner, such that a first strengthening element 74 is adjacent a second strengthening member 76 and in partially overlapping relationship when viewed in the longitudinal direction of the assembly 70. The strengthening members 74, 76 are attached to the tubular substrate 72 by non-conductive posts or elements 78, 80 respectively. In some embodiments, the strengthening members of the first set 74 may be directly connected to the tubular substrate 72 rather than through the posts 78. Annular spacers 82 are located in the annular gaps between the first and second strengthening members 74, 76. The spacer members 82 are made of a non-conductive material and may be flexible to allow relative movement between the sets of spacer members 74, 76, for example during flexing of the assembly 70 as would occur when the catheter assembly is curved through a patient's vasculature. The spacer members 82 hold the strengthening members 74, 76 together in interconnected manner, which contributes to strength of the assembly.

The strengthening members 74, 76 may be a braided wire or of solid metal or metallic material, as with the previously-described embodiments.

In another embodiment, the smaller diameter strengthening members 74 could be connected directly to the tubular substrate 72 with a second tubular substrate positioned to overlie the first strengthening members 74, and with the larger diameter strengthening members 76 positioned to overlie the second tubular support and in longitudinally overlapping interdigitated manner with the first strengthening members 74, as in the embodiment shown in FIG. 8.

It will be appreciated that in another embodiment, the strengthening members 74, 76 could be disposed on the inside of the tubular substrate 72. It will also be appreciated that the spacer members 82 need not be annular and can take any form which will ensure that a gap is maintained between the strengthening members 74, 76. They could, for instance, be in the form of a plurality of distinct spacer blocks arranged around the annular gap between adjacent overlapping strengthening members.

Referring now to FIG. 9, there is shown another embodiment of strengthening assembly 90, which also includes a tubular non-conductive substrate 92 similar to the embodiment of FIG. 8. The assembly 90 includes a series of frusto-conical strengthening members 94 similar to the members 32 of the embodiment of FIGS. 4 and 6. At their narrow ends, the strengthening members 94 are attached to the tubular substrate 92, by bonding, welding or any other suitable method. The strengthening members 94 partially overlap one another and in the space between adjacent members 94. In the region of overlap, there is provided a spacing member 96, which may be of a resilient material and which is non-conductive. Use of a flexible or resilient spacing member 96 provides flexibility to the assembly 90 to enable it to curve within a patient's vasculature.

It will be appreciated that in the embodiments of FIGS. 8 and 9, any torque provided by the strengthening element 70, 90, is at least in part provided by the tubular substrate 72, 92.

Referring now to FIG. 10, there is shown another embodiment strengthening assembly 100, which includes a non-conductive tubular substrate 102 similar to the substrate 72, 92 of the embodiments of FIGS. 8 and 9. A first set of strengthening members 104, made of a metal or metallic material, is disposed within the tubular substrate 102, whereas a second set of strengthening members 106 is disposed on the outside of the tubular substrate 102. The strengthening members 104, 106 may be attached to the substrate 102 by any suitable means, such as bonding, and the like. As will be apparent, the strengthening members 104, 106 are arranged in inter-digitating manner in which a strengthening member of the first set 104 is adjacent strengthening members of the second set 106 and in which the strengthening members 104, 106 partially overlap in the longitudinal direction of the assembly 100.

As with all the previous embodiments, the strengthening members 104, 106 may be made of a braided wire material or of a solid metal or metallic material.

Other embodiments employing the principles taught herein will be apparent to the person skilled in the art.

The embodiments described above are intended to be illustrative only and not limiting of the invention taught herein.

It is also to be understood that the features of the different embodiments described can be combined with one another and that the claims are to be interpreted, even though initially set out in single dependent form, as being combinable as if in multiple dependent form.

The invention claimed is:

1. A catheter strengthening element having a longitudinal dimension and a radial dimension, the strengthening element including a plurality of metallic strengthening members disposed along a common axis, the metallic strengthening members being radially spaced from one another, with adjacent metallic strengthening members partially overlapping one another in the longitudinal direction; the metallic strengthening members being coupled together by at least one non-conductive coupling member,
wherein the non-conductive coupling member couples adjacent metallic strengthening members to one another in an inelastic manner to ensure the overlap between adjacent metallic strengthening members remains, and
wherein the plurality of metallic strengthening members comprises first metallic strengthening members having a first diameter and second metallic strengthening members having a second diameter smaller than the first diameter, and wherein an end of one of the second metallic strengthening members is disposed within a lumen of one of the first metallic strengthening members.

2. A catheter strengthening element according to claim 1, wherein the at least one non-conductive coupling member is operable to transmit torque in at least one of: along the strengthening element, and between metallic strengthening members to which the non-conductive coupling member or members are coupled.

3. A catheter strengthening element according to claim 1, wherein the at least one non-conductive coupling member is made of a polymeric non-conductive material.

4. A catheter strengthening element according to claim 1, including at least one non-conductive spacer member disposed in the radial space between adjacent metallic strengthening members.

5. A catheter strengthening element according to claim 1, wherein the or each non-conductive coupling member is disposed within a region of overlap of adjacent metallic strengthening members, so as to be radially outside one of the metallic strengthening members and radially inside the adjacent metallic strengthening member.

6. A catheter strengthening element according to claim 1, wherein the non-conductive coupling members are annular and are disposed in the radial space between and so as to couple overlapping first and second metallic strengthening members.

7. A catheter strengthening element according to claim 6, wherein the at least one non-conductive coupling member has a length in the longitudinal direction of the element of between 0.5 mm to 2.0 mm.

8. A catheter strengthening element according to claim 1, wherein the non-conductive coupling member is generally tubular and the metallic strengthening members are attached to the tubular non-conductive coupling member.

9. A catheter strengthening element according to claim 1, wherein the metallic strengthening members are frusto-conical elements.

10. A catheter strengthening element according to claim 1, including a tubular non-conductive coupling member and wherein the first and second metallic strengthening members are disposed outside the tubular non-conductive coupling member in a longitudinal arrangement, the first and second metallic strengthening members being attached to the tubular non-conductive coupling member by attachment elements.

11. A catheter strengthening element according to claim 1, wherein the non-conductive coupling member is tubular and wherein the first metallic strengthening members are disposed on the outside of the tube and the second metallic strengthening members are disposed inside the tube and partially longitudinally overlapping the first metallic strengthening members.

12. A catheter strengthening element according to claim 1, wherein adjacent metallic strengthening members longitudinally overlap one another by between 0.5 mm to 2.0 mm.

13. A catheter strengthening element according to claim 1, wherein adjacent metallic strengthening members are radially spaced from one another by between 0.01 mm to 0.5 mm.

14. A catheter strengthening element according to claim 1, wherein the longitudinal overlap of adjacent metallic strengthening members is maintained on curvature of the strengthening element.

15. A catheter strengthening element according to claim 1, wherein the metallic strengthening members and annular non-conductive coupling members form a unitary structure.

16. A catheter assembly including an inner layer providing a catheter lumen, a strengthening element disposed on the inner layer and an outer layer disposed over the strengthening element; the strengthening element having a longitudinal dimension and a radial dimension, the strengthening element including a plurality of metallic strengthening members disposed along a common axis, the metallic strengthening members being radially spaced from one another, with adjacent metallic strengthening members partially overlapping one another in the longitudinal direction; the metallic strengthening members being coupled together by at least one non-conductive coupling member,
wherein the non-conductive coupling member couples adjacent metallic strengthening members to one another in an inelastic manner to ensure the overlap between adjacent metallic strengthening members remains, and
wherein the plurality of metallic strengthening members comprises first metallic strengthening members having a first diameter and second metallic strengthening members having a second diameter smaller than the first diameter, and wherein an end of one of the second metallic strengthening members is disposed within a lumen of one of the first metallic strengthening members.

17. A catheter assembly according to claim 16, wherein the strengthening element provides a layer of the assembly distinct from the inner and outer layers.

18. A catheter assembly according to claim 16, wherein the assembly is one of an introducer sheath, a carrier or delivery catheter, a balloon catheter and a wire guide catheter.

* * * * *

UNITED STATES PATENT AND TRADEMARK OFFICE
CERTIFICATE OF CORRECTION

PATENT NO. : 9,707,373 B2  
APPLICATION NO. : 13/787242  
DATED : July 18, 2017  
INVENTOR(S) : Arne Molgaard Nielsen Page 1 of 1

It is certified that error appears in the above-identified patent and that said Letters Patent is hereby corrected as shown below:

On the Title Page

Left column, item (71), replace "Arne Molgaard Nielsen, Copenhagen (DK)" with --Cook Medical Technologies LLC, Bloomington, IN (US)--.

Left column, item (30), Line 1, under "Foreign Application Priority Data" replace "12275135" with --12275135.7--.

Signed and Sealed this  
Twenty-fourth Day of July, 2018

Andrei Iancu  
*Director of the United States Patent and Trademark Office*